(12) United States Patent
Vayntraub

(10) Patent No.: US 7,901,371 B1
(45) Date of Patent: Mar. 8, 2011

(54) POSTURE CORRECTING BACK BRACE

(76) Inventor: Vladimir Vayntraub, Los Angeles, CA (US)

(*) Notice: Subject to any disclaimer, the term of this patent is extended or adjusted under 35 U.S.C. 154(b) by 297 days.

(21) Appl. No.: 12/273,706

(22) Filed: Nov. 19, 2008

(51) Int. Cl.
*A61F 5/00* (2006.01)
(52) U.S. Cl. .................................. 602/19; 602/4; 602/5
(58) Field of Classification Search ................ 602/4–5, 602/16, 19, 32; 128/874–875
See application file for complete search history.

(56) References Cited

U.S. PATENT DOCUMENTS

| | | | |
|---|---|---|---|
| 1,722,205 A * | 7/1929 | Freund ................................. | 2/44 |
| 2,453,370 A * | 11/1948 | Hittenberger .................... | 602/19 |
| 2,906,260 A * | 9/1959 | Myers .............................. | 602/19 |
| 3,282,264 A * | 11/1966 | Connelly ......................... | 602/19 |
| 4,829,989 A | 5/1989 | Deamer et al. | |
| 5,176,622 A | 1/1993 | Anderson et al. | |
| 5,685,831 A * | 11/1997 | Floyd .............................. | 602/19 |
| 5,816,251 A * | 10/1998 | Glisan ............................. | 128/845 |
| 5,868,691 A | 2/1999 | Vishnevsky | |
| 5,876,361 A | 3/1999 | Harris | |
| 6,280,405 B1 | 8/2001 | Broselid | |
| 6,450,131 B1 * | 9/2002 | Broman ........................ | 119/857 |
| 6,962,572 B1 * | 11/2005 | Zahiri ............................. | 602/19 |
| 2006/0079821 A1 | 4/2006 | Rauch | |

* cited by examiner

*Primary Examiner* — Michael A. Brown
(74) *Attorney, Agent, or Firm* — QuickPatents, Inc.; Kevin Prince

(57) ABSTRACT

The present invention is a device for promoting proper posture in the user wearing the device. The device properly corrects the user's posture when he is slouching his shoulder's forward, and is discrete and comfortable to wear. Two sides of the back plate of the invention are mutually rotatable along a vertical edge which includes a pivot means comprised of a hinge or other device. The back plate further includes a spring means for biasing each side of the back plate away from the user. A pair of shoulder pads each contacts the front side of one of the user's shoulders. The spring means urges each shoulder pad rearward while urging the pivot means of the back plate forward. When the user wearing the invention slouches, the shoulder pads in the invention urge the user's shoulders backwards, thereby correcting the user's posture.

12 Claims, 5 Drawing Sheets

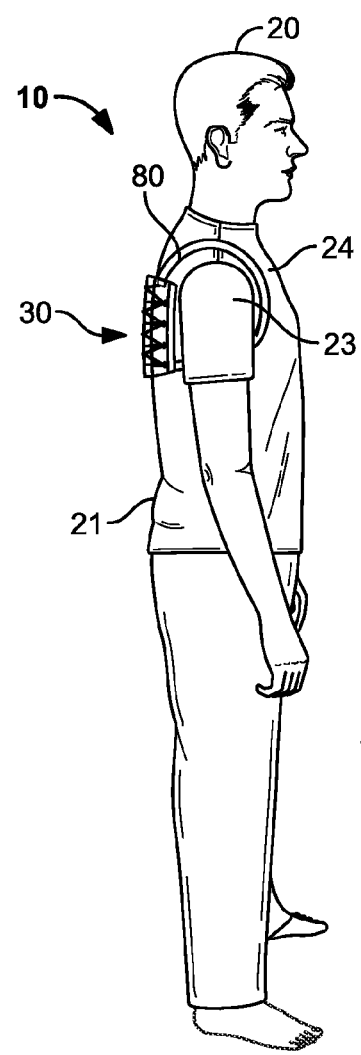
FIG. 1  FIG. 2
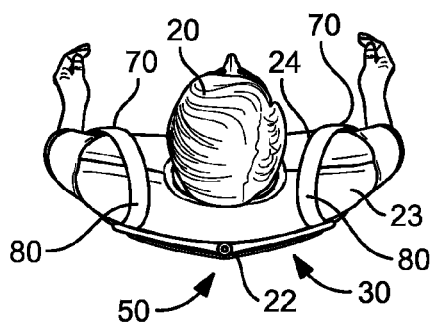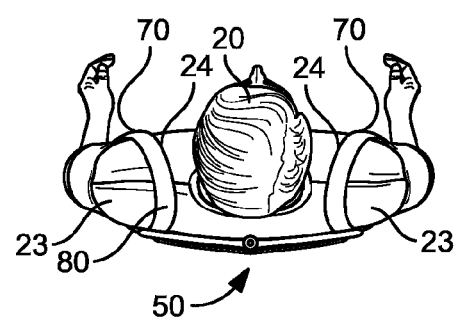
FIG. 3  FIG. 4

POSTURE CORRECTING BACK BRACE

CROSS-REFERENCE TO RELATED APPLICATIONS

Not Applicable.

STATEMENT REGARDING FEDERALLY SPONSORED RESEARCH AND DEVELOPMENT

Not Applicable.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

FIELD OF THE INVENTION

This invention relates to orthopedic back braces, and more particularly to a device for preventing a user from slouching.

DISCUSSION OF RELATED ART

Poor posture is a habitual and difficult to correct problem. It causes a number of adverse effects in the individuals afflicted with it, including certain health problems such as curvature of the spine and a chronic stooping condition. In addition, certain social problems may be experienced by those suffering from poor posture due to the perception that these individuals are lazy, weak, or disinterested in their work.

Various methods to correct poor posture have been devised, some of which are not particularly effective. For example, verbal reminders are usually not the most effective method of correcting poor posture. Instead, various physical devices are more effective to maintain the body in an upright position by training the muscles to maintain proper posture. Physical devices to correct poor posture ideally should be easily attached and removed, and should also be portable and comfortable.

Several prior art devices are known to promote improved posture in those using the devices. For example, U.S. Pat. No. 5,685,831 to Floyd on Nov. 11, 1997, discloses a T-shaped back brace comprised of three interconnected frame members. The vertical and horizontal members are connected at a hinge joint designed to permit free shoulder movement. Straps are utilized to attach the brace to the user's forehead, shoulders and waist. Such a device which attaches to a user's forehead may result in an unsightly appearance and cause negative social perceptions, in addition to being uncomfortable to the user. U.S. Pat. No. 5,868,691 to Vishnevsky on Feb. 9, 1999, discloses a posture training device comprised of a vertical support member and plurality of thin straps inserted through slots in the support member. The straps draw the support member tightly against the user's body causing the user to maintain proper posture.

Some prior art devices are designed to apply pressure to the user's back to improve the user's posture. U.S. Pat. No. 5,876,361 to Harris on Mar. 2, 1999, discloses an exercise and posture correcting device comprised of a bowed strip of spring steel which extends upward from the rear portion of a broad waist belt. A padded contact member connected to the end of the bowed strip with a height adjustable extension sleeve applies pressure to the user's back and thereby maintains his posture.

Finally, the Internet catalog of the Footsmart company, (www.footsmart.com), offers a Posture Enhancing Brace for sale. The Brace utilizes non-elastic straps which are worn around both of the user's shoulders. However the effect of such a brace is to simply pull the user's shoulders together, which does not result in an improvement in the user's posture. In contrast, the present invention actually urges the user's shoulders backwards with respect to his spine in order to correct the user's posture. When the user's posture is correct, the present invention applies no relative force between the user's shoulders and spine. Should the user start to slouch his shoulder's forward, then the spring means contained in the present invention urges the user's shoulder's back and urges his spine forward.

A serious limitation of the prior art devices for correcting posture is that they do not provide three points of contact on the user, i.e. the front of both shoulders and near the spine. For purposes of correcting posture, these points are the only places that need to make resistive contact with the user of a posture correcting device. As such the prior art devices do not properly address the problem of the user slouching his shoulders forward. The prior art devices also tend to be cumbersome and indiscrete. It is relatively easy to make the present invention very discrete and incorporate it into a bra. The prior art devices are not nearly as comfortable to wear as the present invention, particularly when the user is exhibiting proper posture.

Therefore, there is a need for a posture correcting device that would contact the user in the three points described, i.e. the shoulders and the spine, and would also be discrete and comfortable to wear. Such a needed device would properly correct the user's posture when he is slouching his shoulder's forward. The present invention accomplishes these objectives.

SUMMARY OF THE INVENTION

The present invention is a device for promoting proper posture in the user wearing the device. The invention includes a back plate with two sides, where each side is mutually rotatable connected along a vertical edge. The vertical edge of the back plate includes a pivot means which may be comprised of a hinge or other device. The back plate further includes a spring means for biasing a distal side of each side of the back plate away from the user. The back plate is thereby adapted to contact the user's back proximate the user's spine by pressing against it.

The invention includes a pair of shoulder pads, where each shoulder pad is connected with one side of the back plate through a shoulder linkage. In any embodiment the shoulder linkages must completely encircle the user's shoulders. Each shoulder pad thereby contacts the front side of one of the user's shoulders. The spring means urges each shoulder pad rearward while urging the pivot means of the back plate forward. When the user wearing the invention slouches by allowing his shoulders to move forward with respect to his spine, the shoulder pads in the invention urge the user's shoulders backwards with respect to the user's back, thereby correcting the user's posture.

The back plate may be unitary and the pivot means may be comprised of a living hinge. A loop-shaped member may be included in the shoulder linkage which encircles the user's shoulders. The spring means may be comprised of at least one coil spring, or the spring means may be comprised of at least one elastomeric member. Optionally, a resilient padding material may be fixed to the back plate and each shoulder pad.

The invention contacts the user in both shoulders and the spine, and is discrete and comfortable to wear. Further, the needed device properly corrects the user's posture when the user is slouching his shoulder's forward. Other features and advantages of the present invention will become apparent from the following more detailed description, taken in conjunction with the accompanying drawings, which illustrate, by way of example, the principles of the invention.

DESCRIPTION OF THE DRAWINGS

FIG. 1 is a right perspective view of the invention, illustrating a posture improvement device in place on a user;

FIG. 2 is a right perspective view of the invention, illustrating a posture improvement device in place on a user;

FIG. 3 is a top elevational view of the invention in place on a user prior to securing the invention, illustrating the pivot means, should pads, and shoulder linkage;

FIG. 4 is a top elevational view of the invention in place on a user after securing the invention, illustrating the pivot means, should pads, and shoulder linkage;

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions is have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Figure 6:
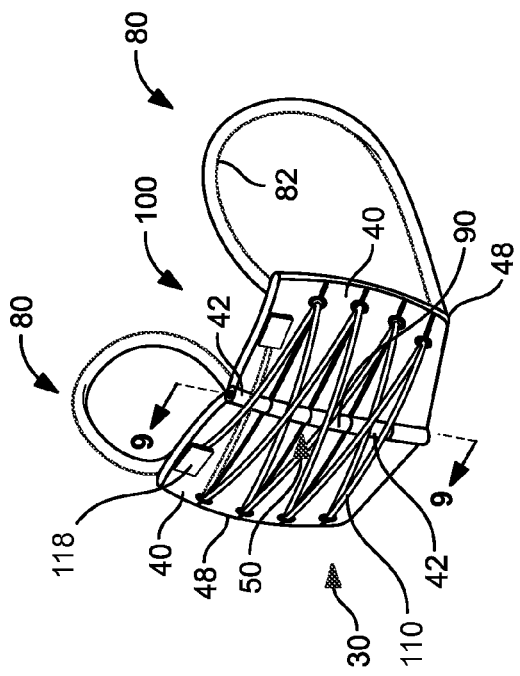
FIG. 6 is a rear perspective view of the invention, illustrating the back plate, the shoulder linkage, and the spring tension adjustment.
Figure 11:
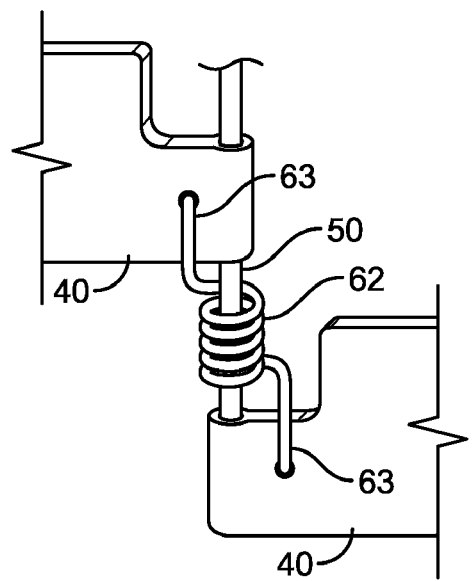
FIG. 11 is a close-up perspective view of the invention, illustrating the pivot means and a coil spring.
Figure 12:
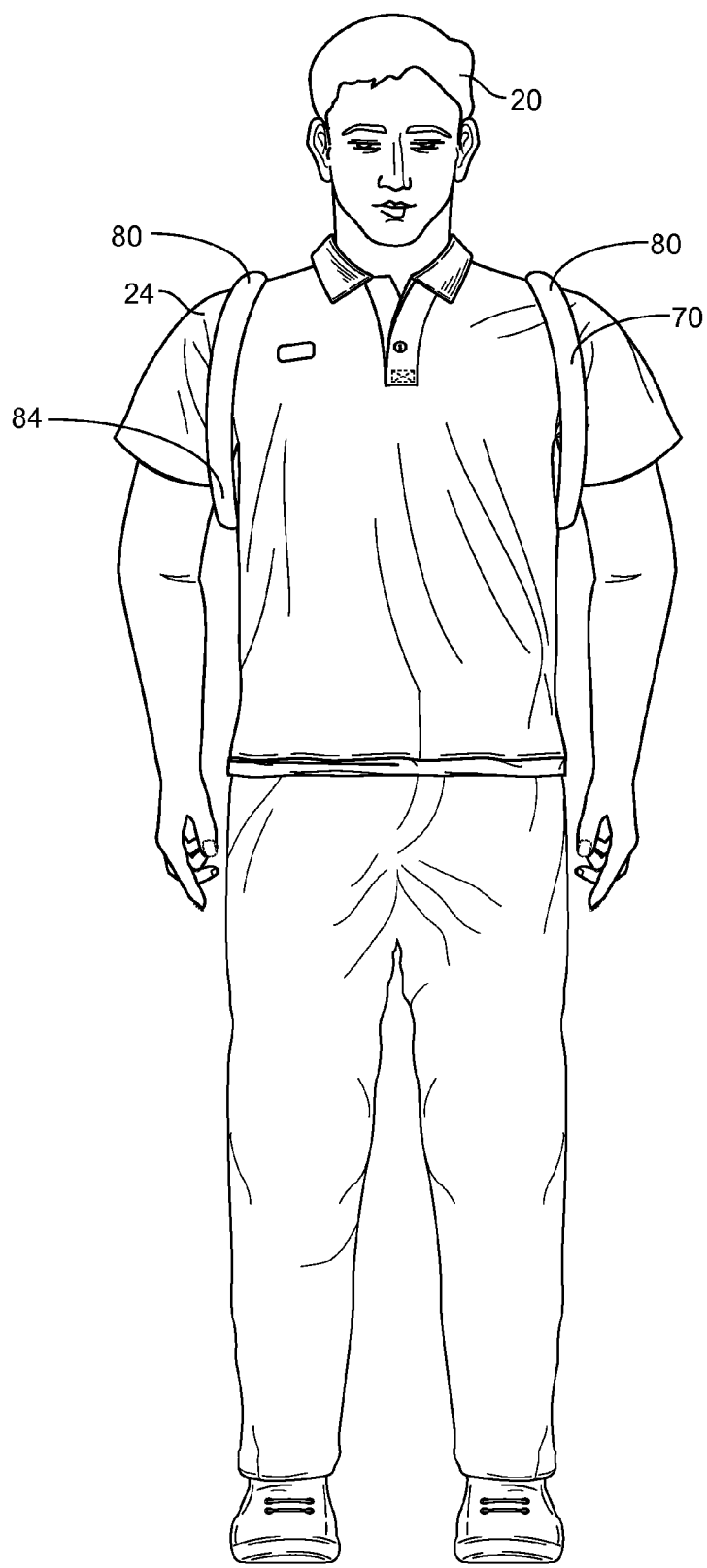
FIG. 12 is a front elevational view of the device illustrated as worn by the user.

The present invention is a device 10 for promoting proper posture in the user 20 wearing the invention. FIG. 6 illustrates the back plate 30 of the invention, including two sides 40, each side 40 mutually rotatably connected along a substantially vertical edge 42. The vertical edge 42 includes a pivot means 50 illustrated in FIG. 11. The back plate 30 further includes a spring means 60 (FIGS. 8 and 9) for biasing a distal side 48 of each side 40 of the back plate 30 away from the user 20. The back plate 30 is thereby adapted to contact the user's back 21 proximate his spine 22 by pressing against it.

Figure 9:
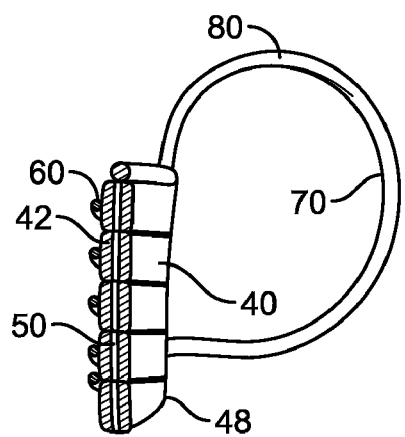
FIG. 9 is a cross-sectional view of the invention, taken generally along lines 9-9 of FIG. 8, and illustrating the right side of the back plate, the pivot means, and a shoulder pad.
Figure 10:
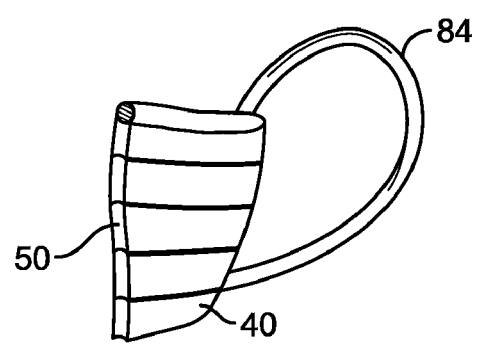
FIG. 10 is a perspective view of the invention, illustrating one side of the back plate and a loop for encircling the user's shoulders.

The invention includes a pair of shoulder pads 70 (FIG. 9), where each shoulder pad 70 is connected with one side 40 of the back plate 30 through a shoulder linkage 80. The shoulder linkages 80 must completely encircle the user's shoulders 23. In one embodiment of the invention illustrated in FIG. 10, the shoulder linkage 80 may include a loop-shaped member 84 which encircles the user's shoulders 23. Each shoulder pad 70 thereby contacts the front side 24 of one of the user's shoulders 23. The spring means 60 urges each shoulder pad 70 rearward while urging the pivot means 50 of the back plate 30 forward. When the user 20 wearing the invention slouches by allowing his shoulders 23 to move forward with respect to his spine 22, the shoulder pads 70 in the invention urge the user's shoulders 23 backwards with respect to the user's back 21, thereby correcting the posture of the user 20.

In the embodiment of the present invention illustrated in FIG. 6 the pivot means 50 is a hinge 90. Alternately, the back plate 30 is unitary and the pivot means 50 may be comprised of a living hinge 92 (FIG. 8), or other hinge means.

Alternately, the spring means 60 may be comprised of at least one coil spring 62 (FIG. 11) having two ends 63, where each end 63 is engaged to one side 40 of the back plate 30. In such an embodiment, the distal edge 48 of each side 40 of the back plate 30 is thereby urged away from the user 20 due to the pressure of the coil spring 62.

Figure 8:
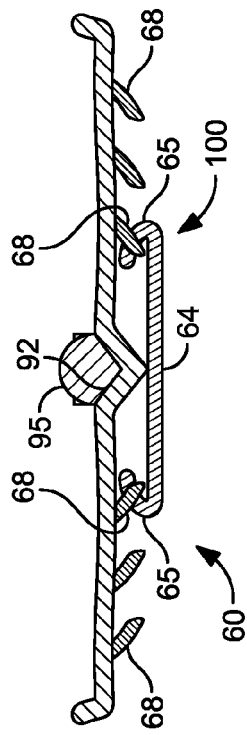
FIG. 8 is a sectional view of the invention, illustrating a spring tension means.

FIG. 8 illustrates an embodiment where the spring means 60 is comprised of at least one elastomeric member 64 having two ends 65. As such, each end 65 is engaged to one side 40 of the back plate 30 thereby urging the distal edge 48 of each side 40 of the back plate 30 away from the user 20.

Figure 13:
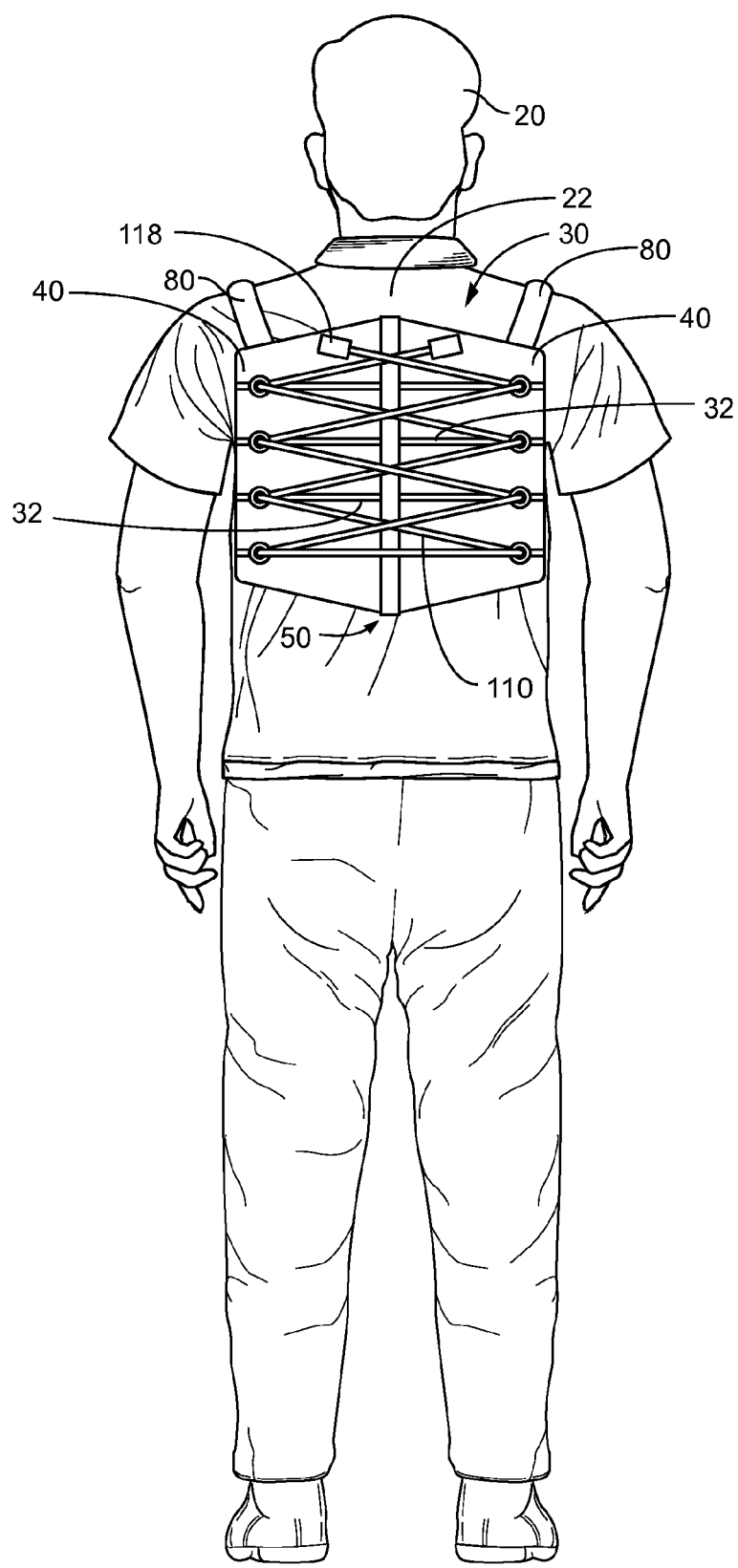
FIG. 13 is a rear elevational view of FIG. 12.

Optionally, a resilient padding material 95 may be fixed to the back plate 30 and may be fixed to each shoulder pad 70 (FIGS. 5, 6 and 8) to soften the pressure on the user's back 21 and the user's shoulders 23. In one embodiment, the back plate 30 is made of a flexible material web or mesh having a plurality of semi-rigid or rigid ribs 32 (FIG. 13). Moreover, the spring means 60 may include a spring tension adjustment means 100 (FIGS. 6 and 8) to allow the user 20 to adjust the spring tension for optimum comfort and effectiveness of the invention.

Turning to FIG. 8, where the spring means 60 is comprised of an elastomeric member 64, at least one end 65 of the elastomeric member 64 may be selectively fixed to any of a plurality of differing tension stops 68. The tension of the spring means 60 may then be adjusted by changing the tension stop 68 where at least one end of the elastomeric member 64 is fixed. In such an embodiment, the substantially vertical edge 42 of each side of the back plate 30 conforms generally to the shape of the user's spine 22 when the user 20 is exhibiting proper posture. The force of the back plate 30 is thereby dissipated onto the user's back 21 when the user 20 is exhibiting proper posture. Alternately, the elastomeric member 64, such as an elastomeric cord, is laced across the back plate 30 such that when pulled taut, the spring tension therein is increased. In such an embodiment, the end of such an elastomeric cord is considered the spring tension adjustment means 100 (FIG. 6). FIG. 6 illustrates an embodiment where the spring tension adjustment means 100 is an elastic adjustment strap 110 selectively fixed to the back plate 30 with a hook-and-loop type fastener 118, mechanical snaps (not shown), or other suitable adjustable attachment means. The adjustment strap 110, in the preferred embodiment, constitutes the spring means 60. The user 20 may thus adjust the spring tension by changing the position of the adjustment strap 110.

Figure 5:
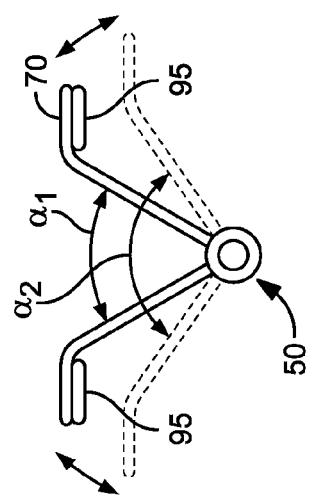
FIG. 5 is a symbolic view of the invention, illustrating the minimum and maximum angles formed between the two shoulder linkages.
Figure 7:
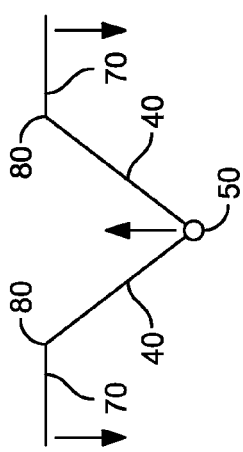
FIG. 7 is a symbolic diagram of the invention, illustrating the forces applied to the user's spine and shoulders by the invention.

The amount of tension generated by the spring means 60 determines an angle $\alpha$ formed between the shoulder linkages 80. FIG. 5 illustrates a minimum angle $\alpha_1$ and a maximum angle $\alpha_2$ formed between the shoulder linkages 80 which connect at the pivot means 50. In FIG. 7 a line diagram shows the direction of the force exerted on the user's spine 22 by the pivot means 50, and the direction of the force exerted on the user's shoulders 23 by the shoulder pads 70.

In one embodiment, rigid or semi-rigid ribs 32 of the back plate 30 may be composed of plastic, bamboo, or other suitable materials, for providing resiliency to the back plate 30. In one embodiment the back plate 30 may be composed of plastic. In other embodiments the back plate 30 may be composed of a flexible fabric. The shoulder linkages 80 may be comprised of flexible straps, semi-rigid rods, or the like.

While a particular form of the invention has been illustrated and described, it will be apparent that various modifications can be made without departing from the spirit and scope of the invention. For example, the spring means 60 may be implemented by a variety of different devices. Accordingly, it is not intended that the invention be limited, except as by the appended claims.

The teachings provided herein can be applied to other systems, not necessarily the system described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the system may vary considerably in its implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A device for promoting proper posture for a user, comprising:
   a back plate having two sides, each side mutually rotatably connected along a substantially vertical edge with a pivot means, the back plate further including a spring means for biasing a distal edge of each side away from the user, the back plate adapted to contact the user's back proximate the user's spine for pressing thereagainst;
   a pair of shoulder pads, each connected with one side of the back plate through a shoulder linkage, each shoulder pad for contacting one of the user's shoulders at a front side thereof, the spring means urging each shoulder pad rearward while urging the pivot means of the back plate forward;
   whereby when the user wearing the device slouches by allowing his shoulders to move forward with respect to his spine, the shoulder pads urge the user's shoulders backwards with respect to the user's back to correct the user's posture.

2. The device of claim 1 wherein the pivot means is a hinge.

3. The device of claim 1 wherein the back plate is unitary and the pivot means is a living hinge therein.

4. The device of claim 1 wherein the shoulder linkage includes a U-shaped member for suspension from the user's shoulders.

5. The device of claim 1 wherein the shoulder linkage includes a loop-shaped member for encircling the user's shoulders.

6. The device of claim 1 wherein the spring means is at least one coil spring having two ends, each end engaged to one side of the back plate to urge the distal edge of each side of the back plate away from the user.

7. The device of claim 1 wherein the spring means is at least one elastomeric member having two ends, each end engaged to one side of the back plate to urge the distal edge of each side of the back plate away from the user.

8. The device of claim 1 further including a resilient padding material fixed to the back plate and each shoulder pad.

9. The device of claim 1 wherein the spring means includes a spring tension adjustment means.

10. The device of claim 9 wherein the spring tension adjustment means is an adjustment strap selectively fixed to the back plate, the adjustment strap coupled to the spring means for changing the position of the spring means to adjust the tension thereof.

11. The device of claim 7, wherein at least one end of the elastomeric member is selectively fixed to any of a plurality of differing tension stops, whereby the tension of the spring means may be adjusted by changing the tension stop to which the at least one end of the elastomeric member is fixed.

12. The device of claim 7 wherein the substantially vertical edge of each side of the back plate conforms generally to the shape of a user's spine when exhibiting proper posture, thereby dissipating the force of the back plate onto the user's back when the user is exhibiting proper posture.

\* \* \* \* \*